United States Patent [19]

Knight et al.

[11] 4,123,274

[45] Oct. 31, 1978

[54] HEAT DEVELOPABLE IMAGING MATERIALS AND PROCESS

[75] Inventors: Phillip D. Knight, Fairport; Richard A. deMauriac, Webster; Patricia A. Graham, Fairport, all of N.Y.

[73] Assignee: Eastman Kodak Company, Rochester, N.Y.

[21] Appl. No.: 778,183

[22] Filed: Mar. 16, 1977

[51] Int. Cl.$^2$ .................. G03C 5/30; G03C 1/02; G03C 1/76; G03C 3/00
[52] U.S. Cl. .................. 96/66 T; 96/114.1; 96/94 R; 96/67
[58] Field of Search .............. 96/114.1, 67, 94 R, 96/95, 56.3, 66 T

[56] References Cited

U.S. PATENT DOCUMENTS

| | | | |
|---|---|---|---|
| 2,353,754 | 7/1944 | Peterson | 96/56.3 |
| 2,710,256 | 6/1955 | Eckler et al. | 96/67 |
| 3,330,663 | 7/1967 | Weyde et al. | 96/94 R |
| 3,554,750 | 1/1971 | Weyde et al. | 96/95 |
| 3,699,114 | 10/1972 | Ohkubo et al. | 96/114.1 |
| 3,767,414 | 10/1973 | Huffman et al. | 96/114.1 |
| 3,785,830 | 1/1974 | Sullivan et al. | 96/114.1 |
| 3,794,496 | 2/1974 | Manhart | 96/114.1 |
| 3,839,041 | 1/1974 | Hiller | 96/114.1 |

OTHER PUBLICATIONS

Chemical Abstracts vol. 23, No. 10, May, 1929 #2178.
Chemical Abstracts vol. 54, Oct., 1960 #19695.

*Primary Examiner*—J. Travis Brown
*Assistant Examiner*—L. Falasco
*Attorney, Agent, or Firm*—Richard E. Knapp

[57] ABSTRACT

A photothermographic material comprising in reactive association (a) photosensitive silver halide, (b) an image-forming combination comprising (i) a silver salt of certain 1,2,4-mercaptotriazole derivatives with (ii) a silver halide developing agent, and (c) a polymeric binder, provides developed images without the need for processing solutions or baths. An image can be developed in this material by merely heating the material to moderately elevated temperatures. The silver salts of certain 3-amino-1,2,4-mercaptotriazole derivatives are particularly preferred compounds. Other addenda employed in heat developable photothermographic materials, such as sensitizing dyes, can be employed with the photothermographic materials described.

32 Claims, No Drawings

HEAT DEVELOPABLE IMAGING MATERIALS AND PROCESS

BACKGROUND OF THE INVENTION

1. Field of the Invention

This invention relates to heat developable imaging materials and processes for developing an image employing in reactive association (a) photosensitive silver halide, (b) an image-forming combination comprising (i) a silver salt of a certain 1,2,4-mercaptotriazole derivative with (ii) a silver halide developing agent, and (c) a polymeric binder. In one of its aspects it relates to a photothermographic element comprising a support having thereon the described photosensitive silver halide and combination of imaging materials. In another aspect it relates to a photothermographic composition comprising the described photosensitive silver halide and imaging combination. A further aspect of the invention relates to a process of developing an image in a photothermographic material containing the described imaging combination. A further aspect relates to new silver salts of certain 1,2,4-mercaptotriazole derivatives, especially those which are useful in the described imaging combination.

2. Description of the State of the Art

It is known to provide an image in an imaging material, especially a photographic imaging material, by what is known as dry processing with heat. These materials are often described as heat developable photographic materials or photothermographic materials. Such heat developable photographic materials after imagewise exposure are heated to moderately elevated temperatures to provide a developed image in the absence of separate processing solutions or baths. Typical heat developable imaging materials or photothermographic materials are described, for example, in U.S. Pat. Nos. 3,152,904 of Sorensen et al, issued Oct. 13, 1964; 3,457,075 of Morgan et al, issued July 22, 1969; 3,392,020 of Yutzy and Yackel, issued July 9, 1968; and British Specification No. 1,161,777 published Aug. 20, 1969.

The most commonly used silver salts in such heat developable photographic materials are silver salts of long-chain fatty acids, such as silver behenate which generally require hydrophobic binders. It has been desirable to replace these silver salts of long-chain fatty acids to enable use of aqueous or hydrophilic compositions which further enable the use of conventional silver halide emulsion technology in heat developable photographic materials. Use of silver behenate as a source of silver in such heat developable materials is not particularly compatible with aqueous formulations of photosensitive silver halide materials. Other silver salts or complexes have been proposed for such heat developable photographic materials. These include, for example, silver salts of benzotriazole, silver salts of saccharin and related silver salts or complexes. These are described, for example, in heat developable photographic materials in U.S. Pat. Nos. 3,617,289 of Ohkubo et al, issued Oct. 2, 1971; 3,666,477 of Goffe, issued May 30, 1972; 3,672,904 of deMauriac, issued June 27, 1972; 3,832,186 of Masuda et al, issued Aug. 27, 1974; British specification No. 1,205,500 published Sept. 16, 1970; 3,689,270 of Anderson et al, issued Sept. 5, 1972; and German Offenlegungsschrift No. 2,326,865 published Dec. 6, 1973. Other silver complexes or salts in heat developable materials, which include silver salts of nitrogen acids, are described in copending U.S. Application Ser. No. 684,699 of deMauriac, filed May 10, 1976, and Research Disclosure, October 1976, Item 15026, pages 18–21, of R. A. deMauriac. While many of these silver complexes or salts can provide an image in such heat developable photographic materials, they often provide poor processing temperature latitude, poor photographic speed, poor image tone, or a combination of one or more of these problems. The photothermographic materials also in many cases have required the presence of what has been described as "melt-forming compound" to provide a desired developed image.

It is desirable in many cases to spectrally sensitize heat developable photographic materials to enable exposure to other than the blue region of the visible spectrum. Difficulty is often encountered in spectrally sensitizing photosensitive silver halide to be used in heat developable materials. While in many cases some degree of spectral sensitization can be provided, it is often insufficient for many photographic purposes. It has been desirable to provide a heat developable silver halide photographic material based on aqueous photographic silver halide technology which permits use of a broader range of spectral sensitizing dyes.

It has also been desirable to provide heat developable photographic materials containing silver salts of certain heterocyclic compounds that enable use of more conventional silver halide developing (reducing) agents in photographic materials. Heat developable photographic materials often have used unconventional reducing agents which require costly processes of preparation. It has been desirable, for instance, to provide heat developable materials which enable use of more conventional hydroquinone silver halide developing agents, 3-pyrazolidone silver halide developing agents and ascorbic acid developing agents. Typical reducing agents which have been used in photothermographic materials are described, for example, in U.S. Pat. No. 3,672,904 of deMauriac, issued June 27, 1972. Commercially available photothermographic materials have contained, for example, 2,2'-methylene bis(4-methyl-6-tertiary butyl phenol) as a reducing agent, but not conventional silver halide developing agents.

Heavy metal salts of certain heterocyclic compounds, such as heterocyclic azoles, are known in thermographic materials, that is materials in which the visible image is formed by imagewise heating, not by a photographic process. Such heavy metal salts of azoles are described, for example, in thermographic materials in U.S. Pat. No. 3,767,414 of Huffman et al, issued Oct. 23, 1973. The described thermographic materials, however, are not photographic materials.

Silver salts of a variety of heterocyclic compounds are known for various purposes in photographic materials. Such uses of silver salts are described, for example, in U.S. Pat. Nos. 2,353,754 of Peterson, issued July 18, 1944 and 3,794,496 of Manhart, issued Feb. 26, 1974.

A common problem encountered in heat developable photographic materials centers on instability of the image following processing. This is usually manifested by print-up following processing. Often heat developable photographic materials have required addition of a separate post-processing image stabilizer or stabilizer precursor to provide desired post-processing stability. Examples of stabilizer precursors in photothermographic materials are described, for instance, in U.S. Pat. No. 3,839,041 of Hiller, issued Oct. 1, 1974. This added component, however, increases the cost of the heat developable material.

There has been a continuing need for improved photothermographic materials which have the improved photosensitivity provided by a photosensitive silver halide material and which enable use of conventional gelatino silver halide emulsion technology. There has also been a continuing need for improved photothermographic materials which enable improved post-processing image stability in the absence of a separate image stabilizer or stabilizer precursor. It has also been desirable to provide a heat developable photographic material as described in which silver development efficiency is improved, such as above about 50%. There has been a further need to provide new silver salts of certain 1,2,4-mercaptotriazole compounds that enable the described advantages in photothermographic materials and processes.

SUMMARY OF THE INVENTION

It has been found according to the invention that the described advantages can be provided in a photothermographic material comprising in reactive association (a) photosensitive silver halide, such as a photosensitive silver halide gelatino emulsion, (b) an image-forming combination comprising (i) a silver salt of a 1,2,4-mercaptotriazole derivative represented by the formula:

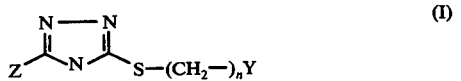

(I)

wherein Y is aryl containing 6 to 12 carbon atoms, such as phenyl, naphthyl, p-chlorophenyl, and p-methoxyphenyl; n is 0 to 2; and Z is hydrogen, hydroxyl or amine (—$NH_2$); with (ii) a silver halide developing agent, and (c) a polymeric binder. Especially useful photothermographic materials as described are those wherein the 1,2,4-mercaptotriazole derivative is one wherein Y is phenyl, p-chlorophenyl or para-methoxy phenyl and Z is amine (—$NH_2$) in the above formula. An image in the described photothermographic material can be provided by merely heating the exposed material at moderately elevated temperatures, such as a temperature within the range of about 140° to 200° C. until the desired image is developed. Certain of the described photothermographic materials can provide not only a developed image, but also a developed image that is stable after processing.

Especially useful photothermographic materials according to the invention are within those described that provide a developed and stabilized image. These especially useful materials include, for example, those described wherein Z is -$NH_2$, n is 1 and Y is phenyl, p-methoxyphenyl or p-chlorophenyl.

It has also been found that certain new silver salts of 1,2,4-mercaptotriazole derivatives are useful in photographic materials. These are silver salts of 1,2,4-mercaptotriazole derivatives represented by the formula:

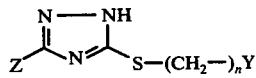

wherein Y is aryl containing 6 to 12 carbon atoms such as phenyl, naphthyl, p-chlorophenyl and p-methoxyphenyl; n is 0 to 2; and Z is hydrogen, hydroxyl or amine (-$NH_2$). An especially useful silver salt within this description is one having a molar ratio of ligand to silver ion within the range of 0.5 to 3.0. These silver salts can be prepared by reacting a source of silver ions, such as silver nitrate and silver trifluoroacetate, with the described 1,2,4-mercaptotriazole derivative.

DETAILED DESCRIPTION OF THE INVENTION

One embodiment of the invention is a photothermographic element comprising a support having thereon in reactive association (a) photosensitive silver halide, (b) an image-forming combination comprising (i) a silver salt of a 1,2,4-mercaptotriazole derivative as described, (ii) a silver halide developing agent, and (c) a polymeric binder. Especially useful silver salts are those within the described formula wherein Y is phenyl, p-chlorophenyl, or para-methoxy phenyl, particularly when Z is -$NH_2$.

An especially useful silver salt in the described photothermographic material is the silver salt of 3-amino-5-benzylthio-1,2,4-triazole.

Combinations of the described silver salts are also useful. The optimum combination of silver salts can be determined based on such factors as the desired image, other components in the photothermographic material, processing conditions, and the like.

It has been found that those compounds in which Y is alkyl instead of aryl according to formula (I) that less than desirable results are obtained in certain photothermographic materials. Specifically, the developed image has the disadvantages that a poor image and undesired fog are obtained.

The 1,2,4-triazole derivatives from which the described silver salts are prepared can be prepared with procedures known in the art. For example, the preparation of 3-amino-5-benzylthio-1,2,4-triazole is carried out with the procedure described in the *Journal of the Chemical Society*, 3437 (1960) by L. Godfrey and F. Kurzer. In this preparation, for example, benzylchloride (139 grams, 1.1 mole) is added dropwise to a mixture of 5-mercapto-3-amino-1,2,4-triazole (116 grams, 1 mole) with 1600 milliliters of ethanol, sodium hydroxide (44 grams, 1.1 mole) and 900 milliliters of water. The reaction mixture is heated at reflux for 6 hours. At the end of this time the ethanol is removed by distillation under reduced pressure; 1000 milliliters of water is added, and the solution is cooled to 5° C. The resulting oil is separated and the desired product crystallized upon cooling. A solid results which is collected and dried in a desiccator. The resulting product can be purified using methods known in the art such as by recrystallization from a suitable solvent such as benzene with sufficient methanol to provide the desired solvent. The resulting 3-amino-5-benzylthio-1,2,4-triazole has a melting point of 108°-109° C.

The silver salt of the described 1,2,4-triazole derivatives can be prepared by mixing a source of silver ions, such as silver trifluoroacetate or silver nitrate with the described 1,2,4-triazole compound until reaction completion. Some heat might be required to solubilize the ligand unless dilute solutions are used. The desired product can be separated by filtration and washing or other known separation techniques. The preparation of the silver salt of 3-amino-5-benzylthio-1,2,4-triazole is illustrative of the preparation of silver salts according to the invention. In this preparation the silver salt is prepared in the form of a dispersion. 6.18 grams (0.03 moles) of 3-amino-5-benzylthio-1,2,4-triazole and 4.0 grams of deionized, photographic gelatin are dissolved with heat at 50° C. into 30 milliliters of a mixture of ethanol and methanol (95:5 parts by volume ethanol:methanol) and 140 milliliters of distilled water. The resulting solution was placed in a suitable reaction vessel equipped with a rapid mixing means and then a solution of 3.4 grams (0.02 moles) of silver nitrate in 30 milliliters of distilled water was added rapidly at 50° C. while the solution was rapidly mixed. The reactants were mixed rapidly for 40 minutes followed by cooling to about 19° C. The resulting desired dispersion was diluted to 200 grams (10 kilograms per silver mole) with distilled water. The end dispersion had a pH of 2.8 and a pAg of 4.6.

It is also useful to prepare the described silver salts of the 1,2,4-triazole derivatives in other compositions than in gelatin as described such as, for example, in poly(vinyl alcohol) or compositions containing no vehicle. Other compositions can be in the form of organic solvent or aqueous solutions or the like. The silver salts also can be separated in their pure form and stored prior to use. However, for photographic purposes it is often useful to prepare the silver salts in the form of a dispersion.

The reactants in the described preparation can be mixed in stoichiometric concentrations. However, it is often desirable to mix one of the components in excess of these concentrations to insure the desired degree of reaction. Typically, for instance, the reactants are mixed to provide a molar ratio of ligand to silver ion of about 1.5. The reaction can be carried out at a temperature within the range of 40° C. to 80° C., typically a temperature within the range of 50° C. to 60° C.

Preparation of the described silver salts is usually not carried out in situ, that is in combination with other components of the photothermographic materials described, but rather is carried out usually ex situ, that is separate from other components of the photothermographic materials. In most instances, the preparation of the silver salts will be separate from the other components of the photothermographic materials based on the ease of control of preparation and storage capability.

The term "salt" as used herein is intended to include any type of bonding or complexing mechanism which enables the resulting material to provide imaging properties in the described photothermographic materials and processing compositions. In some instances the exact bonding of the described silver salt with the 1,2,4-triazole derivative is not fully understood. Accordingly, the term "salt" is intended to include complexes and other forms of bonding which enable the desired image-forming combination to provide the desired image. The term "salt" is intended to include neutral complexes or non-neutral complexes.

The photothermographic materials according to the invention comprise a photosensitive component which is photosensitive silver halide. The photosensitive silver halide is especially useful due to its higher degree of photosensitivity compared to other photosensitive components. A typical concentration of photosensitive silver halide in a photothermographic material according to the invention is within the range of about 0.05 to about 1.0 mole of photosensitive silver halide per mole of the described silver salt of 1,2,4-triazole derivative in the photothermographic material. For example, a typical concentration range of photosensitive silver halide is within the range of 0.1 to about 0.5 mole of photosensitive silver halide per mole of silver salt of 1,2,4-triazole derivative as described in the photothermographic material. Other photosensitive materials can be useful in combination with the described photosensitive silver halide if desired. For example, useful photosensitive silver salts can include photosensitive silver dye complexes such as those described in U.S. Pat. No. 3,647,439 of Bass, issued Mar. 7, 1972. Preferred photosensitive silver halides are silver chloride, silver bromide, silver bromoiodide, silver chlorobromoiodide or mixtures thereof. For purposes of the invention silver iodide is also considered to be useful as a photosensitive silver halide; however, silver iodide is typically more difficult to stabilize after processing at desired levels than silver bromide. Very fine-grain photosensitive silver halide is especially useful although coarse silver halide can be employed. Selection of a suitable reducing agent will be influenced by the grain size and other properties of the particular silver halide grains. For instance, hydroquinone reducing agents are preferred with fine grain silver halides, not coarse grain silver halides. Coarse grain silver halides are not especially useful with hydroquinones as reducing agents. The photosensitive silver halide can be prepared by any of the procedures known in the photographic art, especially those procedures which involve the preparation of photographic silver halide gelatino emulsions. Useful procedures and forms of photosensitive silver halide for purposes of the invention are described, for example, in the *Product Licensing Index*, Volume 92, December 1971, Publication No. 9232 on page 107. Cubic grain silver bromoiodide, such as silver bromoiodide containing 2.5 mole percent iodide can be particularly useful. The photographic silver halide as described can be washed or unwashed, can be chemically sensitized using chemical sensitization procedures and materials known in the art, can be protected against the production of fog and stabilized against loss of sensitivity during keeping as described in the above *Product Licensing Index* publication.

The described photothermographic materials can contain a variety of silver halide developing agents, especially organic silver halide developing agents. Combinations of organic silver halide developing agents can be especially useful. For example, a combination of a 3-pyrazolidone developing agent with an ascorbic acid developing agent can be useful. However, a variety of silver halide developing agents are useful including, for instance, polyhydroxybenzenes, such as hydroquinone, alkyl-substituted hydroquinones, including tertiary butylhydroquinone, methylhydroquinone, 2,5-dimethylhydroquinone, and 2,6-dimethylhydroquinone; catechol and pyrogallol developing agents; chloro-substituted hydroquinones such as chlorohydroquinone or dichlorohydroquinone; alkoxy-substituted hydroquinones such as methoxyhydroquinone or ethoxyhydroquinone; aminophenol reducing agents such as 2,4-diaminophenols and methylaminophenols; ascorbic developing agents such as ascorbic acid, ascorbic acid ketals and ascorbic acid derivatives; 3-pyrazolidone developing agents such as 1-phenyl-3-pyrazolidone and 4-methyl-4-hydroxymethyl-1-phenyl-3-pyrazolidone; reductone silver halide developing agents, such as 2-hydroxy-5-methyl-3-piperidino-2-cyclopentanone; gallic acid ester reducing agents such as methylgallate; sulfonamidophenol developing agents such as the sulfonylamidophenol developing agents described in *Research Disclosure*, January 1973, pages 16-21; phenylenediamine developing agents such as paraphenylenediamine and the like. Especially useful developing agents are those which are hydroquinone, ascorbic acid, pyrogallol, gallic acid ester and phenylenediamine silver halide developing agents and combinations of these developing agents.

The term "silver halide developing agent" as employed herein is intended to include compounds which are developing agent precursors in the described photothermographic materials. That is, those materials which are not developing agents in the photothermographic material until a condition occurs such as heating of the photothermographic material.

A useful concentration of the described developing agent in a photothermographic material according to the invention is typically within the range of about 0.1 mole to about 3 moles of the developing agent per mole of the silver salt of the 1,2,4-triazole derivative as described. An especially useful concentration of developing agent is within the range of about 0.5 to about 1.5 moles of developing agent per mole of silver salt of the 1,2,4-triazole derivative. The optimum concentration of developing agent can be determined based upon factors as the desired image, other components of the photothermographic material, processing conditions and the like.

The photothermographic material according to the invention can contain a variety of colloids and polymers alone or in combination as vehicles, binding agents and in various layers. Suitable materials, as described, are preferably hydrophilic materials although some hydrophobic materials can be useful. The colloids and polymers are transparent or translucent and include both naturally-occurring substances such as proteins, for example, gelatin, gelatin derivatives, cellulose derivatives, polysaccharides, such as dextran and the like; and synthetic polymeric materials such as hydrophilic polyvinyl compounds like poly(vinyl pyrrolidone), acrylamide polymers and the like. Other synthetic polymeric materials that can be employed include dispersed vinyl compounds such as in latex form and particularly those which increase dimensional stability of photographic materials. Effective polymers include high molecular weight materials, polymers and resins which are compatible with the described silver salt of the 1,2,4-triazole derivatives and other components of the photothermographic materials according to the invention. Especially useful materials include gelatin, poly(vinyl pyrrolidone), and poly(vinyl alcohol). Other useful polymeric materials include copolymers of acrylamide with 1-vinylimidazole or 2-acetoacetoxyethylmethacrylate. Combinations of the described colloids and polymers can also be useful.

It is often useful to use one or more of the described polymers or colloids as an overcoat layer or layers on the described photothermographic materials to provide increased resistance to abrasion marks and other advantages.

It is often advantageous to include a base-release agent or base precursor in the photothermographic materials according to the invention to provide improved and more effective image development. A base-release agent or base precursor as employed herein is intended to include compounds which upon heating in the photothermographic material provide a more effective reaction between the described photosensitive silver halide, and the image-forming combination comprising a silver salt of the 1,2,4-mercaptotriazole derivative and the silver halide developing agent. Examples of useful base-release agents or base precursors are guanidinium compounds, such as guanidinium trichloroacetate and other compounds which are known to release a base moiety but do not adversely affect photographic silver halide materials.

A range of concentration of the base-release agent or base precursor is useful in the described photothermographic materials. The optimum concentration of base-release agent or base precursor will depend upon such factors as the desired image, particular components in the photothermographic material, processing conditions and the like. A useful concentration range of base-release agent or base precursor is typically within the range of 0.5 to 1.5 moles of base-release agent or base precursor per mole of silver in the photothermographic material.

The photothermographic materials according to the invention can contain an image toner to provide a more neutral or black tone image upon processing. The optimum toning agent will depend upon such factors as the particular photothermographic material, the desired image tone, particular processing conditions and the like. In some cases certain image toning agents provide better results with certain silver salts of the 1,2,4-mercaptotriazole derivatives than with other silver salts. A simple screening test can be used to select a useful image toning agent. One such test comprises that described in the following Example 5. The silver salt of the 1,2,4-mercaptotriazole derivative in that example can be replaced with other silver salts of the described 1,2,4-mercaptotriazole derivatives to select the optimum image toning agent for the particular silver salt. In this test the most useful toning agent is typically that toning agent that provides the highest ratio of (a) visible maximum density to (b) blue light maximum density. When this ratio exceeds a value of about 0.9, the developed image appears neutral (black). Some toning agents are also found to have other desired effects in the photothermographic material, such as providing development acceleration. Useful toning agents include, for example, 6-methyl-2-thiouracil and 1-phenyl-2-tetraazoline-5-thione. Especially useful toning agents are those which provide a black tone image. Combinations of toning agents can be used if desired.

A range of concentration of toning agent is useful in a photothermographic material according to the invention. A typically useful concentration of toning agent is within the range of about 0.005 to about 0.05 moles of toning agent per mole of silver in the photothermographic material. The optimum concentration of toning agent will depend upon such factors as the particular photothermographic material, processing conditions, desired image, the nature of the toning agent, and the like.

An advantage of the photothermographic materials of the invention containing a silver salt of a 1,2,4-triazole derivative, as described, is that the materials do not require the presence of what is known as a melt-forming compound in order to provide an improved developed image. The term "melt-forming compound" as employed herein is intended to mean a compound which upon heating to the described processing temperature provides an improved reaction medium, typically a molten medium wherein the described image-forming combination can provide better image development. The exact nature of the reaction medium at processing temperatures described is not fully understood; however, it is believed that at the reaction temperatures a melt occurs which permits the reaction components to better interact. If desired, a melt-forming compound can be included with other components of the photothermographic material.

An especially useful embodiment of the invention is a photothermographic element comprising a support having thereon in reactive association (a) photosensitive silver halide, typically a photographic silver halide gelatino emulsion, (b) an image-forming combination comprising (i) a silver salt of 3-amino-5-benzylthio-1,2,4-triazole, and (ii) a silver halide developing agent, as described, (c) a polymeric binder, typically a gelatino binder, and (d) an image toner, also as described.

Another especially useful embodiment of the invention is a photothermographic element as described above wherein the silver salt of 3-amino-5-benzylthio-1,2,4-triazole is replaced with the silver salt of 3-amino-5-(p-methoxy) benzylthio-1H-1,2,4-triazole.

A further especially useful embodiment of the invention is a photothermographic element as described above wherein the silver salt of 3-amino-5-benzylthio-1,2,4-triazole is replaced with 3-amino-5-(p-chloro)benzylthio-1,2,4-triazole.

Spectral sensitizing dyes can be useful in the described elements and compositions of the invention to confer additional sensitivity to the elements and compositions. Useful sensitizing dyes are described, for example, in the *Product Licensing Index*, Volume 92, December 1971, Publication No. 9232, pages 107-110, paragraph XV. An advantage of the photothermographic materials according to the invention is that a range of spectral sensitizing dyes is useful. In many heat developable photographic materials the range of useful spectral sensitizing dyes is often undesirably limited. This advantage of the photothermographic materials of the invention is due in part to the fact that the photothermographic materials of the invention enable use of conventional silver halide emulsions. Selection of an optimum spectral sensitizing dye or dye combination will depend upon such factors as the particular silver halide used, the desired spectral sensitivity, and the like.

A preferred photothermographic material according to the invention contains a spectral sensitizing dye selected from the group consisting of cyanines and merocyanines and combinations of these dyes. Especially useful dyes include:
  thiacarbocyanine dyes,
  merocyanine dyes containing a rhodanine moiety,
  solubilized oxacarbocyanine dyes,
  oxacarbocyanine dyes, and
  merocyanine dyes containing a 2-thio-2,4-oxazolidinedione moiety.

A range of concentration of spectral sensitizing dye or dye combination is useful in the described photothermographic materials. Typically, the spectral sensitizing dye concentration is within the range of 0.5 to 2.0 grams of dye per mole of silver halide.

The optimum concentration of the various components of the photothermographic material according to the invention will depend upon a variety of factors as described. An especially useful photothermographic material according to the invention comprises, for each mole of photosensitive silver halide, 2.0 to 8.0 moles of the described silver salt of the 1,2,4-mercaptotriazole derivative, and 5.0 to 10.0 moles of the described silver halide developing agent.

The silver salt of the described 1,2,4-mercaptotriazole derivative can contain a range of ratio of the 1,2,4-mercaptotriazole moiety to the silver ion. The optimum ratio of the triazole moiety to silver ion will depend upon the particular 1,2,4-mercaptotriazole derivative, the particular photothermographic material, processing conditions and the like. However, the molar ratio of the 1,2,4-mercaptotriazole moiety to silver as silver ion in the salt is usefully within the range of 0.5 to 3.0. The 1,2,4-mercaptotriazole moiety is referred to herein as the ligand. As especially useful ratio of the described 1,2,4-mercaptotriazole moiety to silver as silver ion is 1.5.

The photothermographic materials of the invention also can contain a range of pAg. The pAg can be measured using conventional calomel and silver-silver chloride electrodes, connected to a commercial digital pH meter. The typical pAg in a dispersion containing the described components according to the invention is within the range of about 2.5 to about 7.5, with a preferred range of pAg being 4.0 to 5.0. The optimum pAg will depend upon the described factors, such as the particular photothermographic material, desired image, processing conditions and the like.

A dispersion containing the described components according to the invention typically has a pH range which is about 1.5 to 5.0. An especially useful pH for a dispersion as described is within the range of about 2.0 to 4.0 with the preferred range being about 2.5 to 3.5.

An advantage of certain of the photothermographic materials according to the invention is that no separate post-processing image stabilizer or stabilizer precursor is required in these certain photothermographic materials. However, a stabilizer or stabilizer precursor can be employed in any of the photothermographic materials described according to the invention if desired. Such stabilizers or stabilizer precursors include sulfur compounds which upon heating of the photothermographic material form a stable mercaptide in the non-image areas of the photothermographic material. Also, photolytically activated polyhalogenated compounds can be used, but these compounds have been found to be less desirable than other stabilizers or stabilizer precursors in situations in which an added stabilizer or stabilizer precursor is desired.

The photothermographic materials according to the invention can contain other addenda such as development modifiers that function as speed-increasing compounds, hardeners, plasticizers and lubricants, coating aids, brighteners, absorbing and filter dyes, antistatic materials or layers, and the like. These are described, for example, in the *Product Licensing Index*, Volume 92, December 1971, Publication 9232, pages 107-110.

The photothermographic elements according to the invention can comprise a variety of supports which can tolerate the processing temperatures employed according to the invention. Typical supports include cellulose ester film, poly(vinyl acetal) film, poly(ethylene terephthalate) film, polycarbonate film and polyester film supports as described, for example, in U.S. Pat. No. 3,634,089 of Hamb, issued July 11, 1972 and U.S. Pat. No. 3,725,070 of Hamb et al, issued Apr. 3, 1973. Related film and resinous support materials, as well as glass, paper, metal and the like supports which can withstand the processing temperatures described, are also useful. Typically, a flexible support is most useful.

The photothermographic materials according to the invention can be coated on a suitable support by various coating procedures known in the photographic art including dip coating, air knife coating, curtain coating or extrusion coating using hoppers such as described in U.S. Pat. No. 3,681,294 of Beguin, issued June 15, 1954.

If desired, two or more layers can be coated simultaneously such as described in U.S. Pat. No. 2,761,791 of Russell, issued Sept. 4, 1956 and British Pat. No. 837,095 published June 9, 1960.

The described components of the photothermographic materials according to the invention can be in any suitable location in the photothermographic materials which provides the desired image. For example, if desired, one or more of the components of the photothermographic element described can be in one or more layers of the element. In some cases it can be desirable to include certain percentages of the described silver halide developing agent, silver salt of the 1,2,4-mercaptotriazole derivative and/or other addenda in a protective layer over the photothermographic layer as described. The components must be in a location which enables their desired interaction upon processing.

It is necessary that the photosensitive silver halide, as described, and other components in the image-forming combination be in reactive association with each other in order to provide the desired image. The term "in reactive association", as employed herein, is intended to mean that the photosensitive silver halide and the image-forming combination are in a location with respect to each other which enables the desired processing and provides a useful developed image. It is believed that the latent image formed upon imagewise exposure of the photosensitive silver halide acts as a catalyst for the image-forming combination containing the silver salt of the described 1,2,4-mercaptotriazole derivative. While the exact nature of the reaction mechanisms and image formation in the photothermographic material described is not fully understood, it is believed that the reaction is an amplification reaction enabled by the catalytic effect of the latent image silver.

If desired, other heat developable photographic materials or photothermographic materials can be used in combination with the photothermographic materials according to the invention. The other heat developable photographic materials or photothermographic materials must be compatible with and not adversely affect the image formation in a photothermographic material according to the invention. For example, a photothermographic element can comprise respectively a support having thereon a heat developable photographic layer comprising photosensitive silver halide in reactive association with an image-forming combination comprising (i) a silver salt of a 3-amino-1,2,4-mercaptotriazole derivative as described with (ii) a silver halide developing agent according to the invention and a separate layer containing a different photothermographic material containing photosensitive silver halide as a component with other necessary imaging materials. An example of such a photothermographic material is one containing a layer contiguous to the layer containing the silver salt of the 1,2,4-mercaptotriazole derivative and which separate layer contains photosensitive silver halide in reactive association with a silver salt of certain heterocyclic thione compounds and an organic reducing agent. A useful heat developable photographic material containing such a silver salt of certain heterocyclic thione compounds is described in U.S. Pat. No. 3,893,860 of Sutton et al, issued July 8, 1975. In some cases the silver salt of the heterocyclic thione compound as described in U.S. Pat. No. 3,893,860 can be used in the same layer as the described silver salt of the 1,2,4-mercaptotriazole derivative. The optimum concentrations and ratios of components in these layers will depend upon the desired image, particular components of the photothermographic material, processing conditions and the like.

Another embodiment of the invention is a photothermographic composition comprising (a) photosensitive silver halide and (b) an image-forming combination as described. An especially useful composition is one containing a polymeric binder, also as described.

A variety of imagewise exposure means can be used with the photothermographic materials according to the invention. The materials are typically sensitive to the ultraviolet and blue regions of the spectrum and exposure means which provide this radiation are preferred. Typically, however, if a spectral sensitizing dye is employed in the photothermographic materials, exposure means using other ranges of the spectrum are applicable. Typically, a photothermographic element according to the invention is exposed imagewise with a visible light source, such as a tungsten lamp, although other sources of radiation are useful, such as lasers, electron beams, X-ray sources and the like. The photothermographic materials are typically exposed imagewise to provide a developable latent image.

A visible image can be developed in a photothermographic material, as described, within a short time, such as within several seconds, merely by uniformly heating the photothermographic material to moderately elevated temperatures. For example, the exposed photothermographic material can be heated to a temperature within the range of about 125° to 200° C., typically 150° to 180° C. Heating is carried out until a desired image is developed, typically within about 1 to about 60 seconds, such as within 1 to 30 seconds. At the lower processing temperatures, such as at about 125° C., development of an image requires a longer processing time. However, at the lower processing temperatures, such as below about 140° C., post-processing stabilization will not be observed with the described photothermographic materials that contain the preferred silver salts also as described.

Another embodiment of the invention is a process of developing and stabilizing an image in an exposed photothermographic material as described containing the preferred silver salts of 1,2,4-triazole derivatives comprising heating the photothermographic material to a temperature within the range of 140° C. to 200° C. until an image is developed and stabilized.

An especially useful process according to the invention comprises developing and stabilizing an image in a photothermographic element comprising a support having thereon in reactive association (a) photosensitive silver halide, (b) an image-forming combination comprising (i) a silver salt of a 1,2,4-triazole derivative that is 3-amino-5-benzylthio-1,2,4-triazole, 3-amino-5-(p-methoxy)benzylthio-1H-1,2,4-triazole or 3-amino-5-(p-chloro)benzylthio-1,2,4-triazole, or combinations thereof, and (ii) a silver halide developing agent, (c) a polymeric binder and (d) an image toner, as described, comprising heating the described element to a temperature within the range of about 140° to about 200° C. until a desired image is obtained, such as for about 1 to about 30 seconds.

Although it is often undesirable, due to the lack of control in preparation, the described photosensitive silver halide can be prepared in situ in the described material according to the invention. Such a method of preparation of photosensitive silver halide in situ in a photothermographic material is described, for example, in U.S. Pat. No. 3,457,075 of Morgan et al, issued July 22, 1969.

Processing according to the invention is usually carried out under ambient conditions of pressure and humidity. Pressures and humidity outside normal atmospheric conditions can be employed if desired; however, normal atmospheric conditions are preferred.

A variety of means can be employed to provide the necessary heating of the described photothermographic materials to provide a developed and stabilized image. The heating means can be a simple hot plate, iron, roller or the like.

The following examples are included for a further understanding of the invention.

EXAMPLE 1

A. Preparation of 3-amino-5-benzylthio-1,2,4-triazole

A. Benzyl chloride (139 grams, 1.1 mole) was added dropwise to a mixture of 5-mercapto-3-amino-1,2,4-triazole (116 grams, 1 mole), 1600 milliliters of ethanol, sodium hydroxide (44 grams, 1.1 mole) and 900 milliliters of water. The reaction mixture was then heated at reflux for 6 hours. At the end of this time the ethanol was removed by distillation under reduced pressure, 1000 milliliters of water was added, and the solution was cooled to 5° C. The resulting oil which separated crystallized upon cooling. The resulting solid was collected, dried in a dessicator and recrystallized from 1200 milliliters of benzene with enough methanol to effect solution. The desired white solid product was obtained having a melting point of 108°–109° C. The desired product was also identified through mass spectrum analysis and nuclear magnetic resonance analysis.

The following 1,2,4-mercaptotriazole derivatives were also prepared using a technique similar to that described above for preparation of 3-amino-5-benzylthio-1,2,4-triazole:

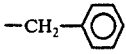

B. Preparation of 3-amino-5-phenylmercapto-1,2,4-triazole

Diphenyliodonium bromide (120 g., 0.33 mole) was added to a solution of 3-amino-5-mercapto-1,2,4-triazole (38.2 g., 0.33 mole) and sodium methoxide (17.8 g., 0.33 mole) in 700 ml of methanol. The resulting mixture was stirred at reflux for five days. The reaction mixture was then evaporated to dryness. The residue was taken up in water and extracted twice with ethoxy acetate. The combined organic extracts were dried over magnesium sulfate, filtered and evaporated to dryness. The residue was slurried in CHCl₃ and filtered. The crude product was adsorbed on a silica dry column with ethoxy acetate as solvent. The product band was excised and extracted with ethanol. The extract was evaporated to dryness and the residue slurried in CHCl₃ and filtered. The product was then recrystallized from a mixture of ethoxy acetate and CHCl₃ to provide a white solid having a melting point of 144°–146° C. The product was identified by mass spectroscopy and nuclear magnetic resonance.

C. Preparation of silver salts of 1,2,4-triazole derivatives 6.18 grams (0.03 moles) of 3-amino-5-benzylthio-1,2,4-triazole (also referred to herein as ABT) and 4.0 grams of deionized, photographic gelatin were dissolved with heating into 30 milliliters of a solvent consisting of 95 parts by volume ethanol and 5 parts by volume methanol and 140 milliliters of distilled water. To this solution in a water jacketed, stainless steel mixer, held at about 50° C., was rapidly added a solution of 3.4 grams (0.02 mole) of silver nitrate in 30 milliliters of distilled water while rapidly mixing the composition. The mixing speed was quickly increased and the composition was thoroughly mixed for a period of 40 minutes. The composition was then cooled to about 19° C. The final desired dispersion contained the silver salt of 3-amino-5-benzylthio-1,2,4-triazole and was adjusted to 200 grams by addition of distilled water. The composition weight was 10 kilograms per silver mole. The resulting dispersion had a pH of 2.8 and a pAg of 4.6.

Silver salts of the above 1,2,4-triazole derivatives listed in 1A were prepared in a similar manner.

EXAMPLE 2

Photothermographic material containing the silver salt of 3-amino-5-benzylthio-1,2,4-triazole A photothermographic composition was prepared by mixing the following components:

| | |
|---|---|
| silver salt dispersion contaning the silver salt of 3-amino-5-benzylthio-1,2,4-triazole (ABT) as described from Example 1C | 4.0 ml |
| silver bromoiodide gelatino emulsion (2.5 mole percent iodide, 0.06 micron size, diluted 1:4 with distilled water). (The emulsion was diluted to provide about 13 mg. of Ag per ml.). | 0.7 ml |
| hydroquinone (10% by weight in methanol) | 0.7 ml |
| surfactant (Surfactant 10G which is a para-isononylphenoxypolyglycidol surfactant available from the Olin Co., U.S.A.) (10% by weight in distilled water) | 0.2 ml |
| distilled water | 2.4 ml |

The resulting composition after mixing was coated on a polyethylene coated paper support at a wet coating thickness of 4 mils. The coating was prepared using a coating apparatus at a temperature of about 45° C. The resulting photothermographic element was permitted to dry with the aide of a source of warm air. This provided a photothermographic element according to the invention. The resulting element was then imagewise exposed with a flash exposure to light through a 0.3 incremental step tablet. The resulting latent image in the element was developed by heating the element on a metal block at 175° C. for 30 seconds. A brown-black tone image was developed having 6 process steps with a white background. The resulting developed image provided a visual reflection maximum density of 1.11 and a minimum density of 0.06.

The image and background areas of the photothermographic element were stable to light when exposed for 24 hours at 120 foot candles of exposure.

EXAMPLE 3

This is a comparative example.

The silver salts of the following compounds were compared in a composition like that described in Example 2:

3-amino-1,2,4-triazole (3NH$_2$);
5-benzylthio-1,2,4-triazole (BTT);
and 3-amino-5-benzylthio-1,2,4-triazole (ABT).

A dispersion with each of the above compounds was prepared in the same manner as described in Example 1C with a ligand to silver ion molar ratio in each instance of 1.5:1. The dispersion weight was 10 kilograms per silver mole and contained 200 grams of gelatin per silver mole. The dispersion containing the 3NH$_2$ silver salt had a pH of 3.4 and a pAg of 4.3. The dispersion containing the silver salt of the BTT compound had a pH of 1.9 and a pAg of 2.9. The dispersion containing the silver salt of the ABT compound had a pH of 2.8 and a pAg of 4.6.

The photothermographic compositions containing the described silver salts were identical and prepared by coating the compositions at a 4 mil wet coating thickness on a paper support. The coating composition contained the following components:

| | |
|---|---|
| silver salt dispersion as described (5.5 milligrams of silver per square decimeter) | 4.0 ml |
| silver bromoiodide gelatino emulsion (the same emulsion as in Example 2) (1.2 milligrams of silver per square decimeter) | 0.7 ml |
| hydroquinone (10% by weight in distilled water) (8.9 milligrams per square decimeter) | 0.7 ml |
| surfactant (Surfactant 10G, 10% by weight in distilled water) | 0.2 ml |
| distilled water | 2.4 ml |

The photothermographic composition in each instance was permitted to dry to provide a photothermographic element. The resulting elements were identically exposed to provide a developable latent image using a commercial sensitometer. The photothermographic element in each instance was then heated on a metal block at temperatures within the range of 145° C. to 200° C. for 30 seconds. The densities of the developed images in each instance were observed with blue light using a commercial reflection densitometer and then placed in a container and exposed to light for 24 hours at 130 foot candles of illumination. After this period of time the densities were again observed with a densitometer. The results in each instance are listed in the following Table I.

Table I

| Ligand | Process Temperature (° C) | | | | | |
|---|---|---|---|---|---|---|
| | 145 | 155 | 165 | 175 | 185 | 200 |
| 3NH$_2$ D$_{max}$ | 1.00 | 1.01 | 1.03 | 1.05 | 1.05 | 1.05 |
| D$_{min}$ | 0.27 | 0.27 | 0.29 | 0.24 | 0.30 | 0.34 |
| D$_{min\ (print-up)}$ | 0.75 | 0.80 | 0.51 | 0.38 | 0.37 | 0.42 |
| $\Delta$D$_{min}$* | 0.48 | 0.53 | 0.22 | 0.14 | 0.07 | 0.08 |
| BTT D$_{max}$ | 0.49 | 0.48 | 0.52 | 0.59 | 0.58 | 0.60 |

Table I-continued

| Ligand | Process Temperature (° C) | | | | | |
|---|---|---|---|---|---|---|
| | 145 | 155 | 165 | 175 | 185 | 200 |
| D$_{min}$ | 0.23 | 0.23 | 0.19 | 0.16 | 0.17 | 0.18 |
| D$_{min\ (print-up)}$ | 0.80 | 0.79 | 0.73 | 0.31 | 0.33 | 0.26 |
| $\Delta$D$_{min}$* | 0.57 | 0.56 | 0.54 | 0.15 | 0.16 | 0.08 |
| ABT D$_{max}$ | 1.38 | 1.35 | 1.41 | 1.38 | 1.33 | 1.18 |
| D$_{min}$ | 0.14 | 0.13 | 0.13 | 0.11 | 0.12 | 0.17 |
| D$_{min\ (print-up)}$ | 0.89 | 0.66 | 0.67 | 0.17 | 0.15 | 0.21 |
| $\Delta$D$_{min}$* | 0.75 | 0.53 | 0.54 | 0.06 | 0.03 | 0.04 |

*$\Delta$D$_{min}$ means the difference between (i) the minimum density value listed and observed before the photothermographic element is tested for light stability and (ii) the minimum density value observed after the light stability test and listed as D$_{min\ (print-up)}$.

The data in Table I illustrates that the photothermographic element containing the silver salt of ABT provided higher maximum density, lower minimum density and at temperatures of processing over 175° C. provided less increase in minimum image density.

EXAMPLE 4

Addition of image toner

A dispersion was prepared as described in Example 1C with the silver salt of ABT with the exception that the silver salt contained a ligand to silver ion molar ratio of 1.0. A photothermographic composition was prepared as described in Example 2 with the exception that an equal molar concentration of tertiary-butylhydroquinone was used in place of hydroquinone as the silver halide developing agent. The photothermographic composition was coated as described in Example 2, imagewise exposed and the resulting latent image developed as described in Example 2. A brown-black developed image with a visual to blue light maximum reflection density ratio of 0.73 was obtained. The developed image had a maximum visual reflection density of 0.89 and a reflection maximum density to blue light of 1.21. A perfectly neutral image is considered to have a visual to blue light maximum reflection density ratio of 1.0.

The described procedure was repeated with the exception that 0.6 milliliters of a 0.125 percent by weight solution of 6-methyl-2-thiouracil in methanol was added as an image-toning agent. The resulting developed image had a visual to blue light maximum reflection density ratio of 0.81 (1.06 maximum density to visual light and 1.31 maximum density to blue light). The developed image appeared gray-black.

This illustrates that image tone was improved by the use of the described toning agent. No significant adverse affects on the stability of the processed material were observed.

EXAMPLE 5

Use of 1-phenyl-2-tetraazoline-5-thione as a toning agent

A dispersion was prepared as described in Example 1C with the silver salt of ABT with the exception that the ligand to silver ion molar ratio in this silver salt was 1.6. A photothermographic composition was prepared using the coating composition described in Example 2 with the exception that an equal molar amount of tertiary-butylhydroquinone was used in place of hydroquinone as the silver halide developing agent. The photothermographic composition was coated on a paper support as described in Example 2. The resulting photothermographic element was exposed and processed as described in Example 2 to provide a developed image. The resulting developed image had a visual to blue light maximum reflection density ratio of 0.73 (maximum density of 0.83 to visual light and a maximum density of 1.13 to blue light).

The procedure was repeated with the exception that 0.33 milliliters of a 0.25% by weight solution of 1-phenyl-2-tetraazoline-5-thione in ethanol was added as an image-toning agent. The resulting developed image provided a visual to blue light maximum reflection density ratio of 0.91 (a maximum density of 1.12 to visual light and a maximum density of 1.23 to blue light). The developed image appeared neutral (black).

This illustrated that both the maximum reflection density and image tone were improved with the addition of the described toning agent.

EXAMPLE 6

Processing temperature latitude with the silver salt of ABT

The dispersion described in Example 1C was used containing the silver salt of ABT. A photothermographic composition was prepared as described in Example 2 with the exception that an equal molar concentration of tertiarybutylhydroquinone was used in place of hydroquinone. The photothermographic composition was coated on a paper support as described in Example 2. The resulting photothermographic element was imagewise exposed and processed also as described in Example 2 with the processing temperature and time as listed in following Table II. The resulting developed image had a maximum and minimum visual reflection density as described in following Table II.

Table II

| Process Temperature and Time | $D_{max}/D_{min}$ | 6th Step Density |
|---|---|---|
| 155° C/30 sec. | 0.92/0.06 | 0.40 |
| 165° C/30 sec. | 0.97/0.05 | 0.49 |
| 175° C/30 sec. | 0.99/0.06 | 0.42 |

The data in Table II illustrates that no significant change in photographic speed or maximum and minimum density is observed over the temperature range of processing as described.

EXAMPLE 7

Chemically sensitized silver halide in photothermographic materials according to the invention The dispersion described in Example 1C was employed for this example. A photothermographic composition was prepared as described in Example 2 with the exception that an equal molar concentration of tertiary-butylhydroquinone was used in place of hydroquinone as the developing agent.

A photothermographic element was prepared with this composition as described in Example 2. The photothermographic element was imagewise exposed to light and the resulting latent image was developed and stabilized by heating the element on a metal block at 175° C. for 30 seconds. The resulting developed image provided 7 developed steps with a visual reflection maximum density of 0.99 and a minimum density of 0.06.

The procedure was repeated with the exception that a silver halide gelatino emulsion of the same grain size was used having sulfur and gold chemical sensitization in place of the silver halide described in Example 2. The resulting developed image had a maximum reflection density of 1.02 and a minimum density of 0.10 with 9 density steps.

The chemically sensitized emulsion resulted in increased photographic speed.

EXAMPLE 8

Spectral sensitization of a photothermographic material containing the silver salt of ABT The dispersion as described in Example 2 containing the silver salt of ABT was used in this example. A photothermographic composition containing this dispersion was prepared as described in Example 2. This composition was coated on a paper support to provide a photothermographic element as described in Example 2. The resulting element was imagewise exposed and processed as described in Example 7 to provide a developed image having a maximum reflection density to visual light of 0.92 and a minimum density of 0.07 with 7 visible image steps.

The procedure was repeated with the exception that a spectral sensitizing dye (1.5 grams of dye per silver mole) represented by the formula:

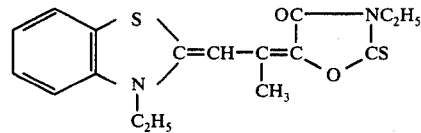

was used in the described silver halide emulsion. The resulting developed image had a maximum reflection density of 0.97 and a minimum reflection density of 0.08 with 11 developed steps. No evidence was observed of undesirable dye stain in the background areas of the processed material.

EXAMPLE 9

Use of higher ligand to silver ion ratios in a photothermographic material

A dispersion containing the silver salt of ABT was used in this example as described in Example 1C except at a ligand to silver ion ratio of 1.2 and 100 grams of gelatin per silver mole. The photothermographic composition was prepared by mixing the following components:

| | |
|---|---|
| silver salt dispersion (prepared as described in Example 1C) | 4.0 ml |
| silver bromoiodide gelatino emulsion (2.5 mole % iodide, 0.06 micron size, diluted 1:4 with distilled water). (The emulsion was diluted to provide about 13 mg. of Ag per ml.). | 0.7 ml |
| hydroquinone (10% by weight in methanol) | 0.7 ml |
| surfactant (Surfactant 10G, 10% by weight in distilled water) | 0.2 ml |
| 3-amino-5-benzylthio-1,2,4-triazole (10% by weight in methanol) | 0.7 ml |
| distilled water | 1.7 ml |

The final ligand to silver ion molar ratio in the photothermographic composition was 2.0. The composition was coated at a 4 mil wet coating thickness on a paper support. The photothermographic layer was permitted to dry and then was imagewise exposed as described in Example 4. The exposed element was then heated by contacting it with a metal block at 145° C. for 30 seconds. A red-brown developed image was produced having 6 density steps with a maximum visual reflection density of 0.70 and a minimum density of 0.08. In addition, the background density (minimum density) of the processed material increased only 0.01 density units upon re-exposure to light for 24 hours at 130 foot candles.

This indicated that increasing the ligand to silver ion ratio from 1.5 to 2.0 provided increased post-processing light stability with about 30° C. lower processing temperature.

EXAMPLE 10

Use of base-release agent or base precursor

The dispersion containing the silver salt of ABT as described in Example 1C was used in this example. A photothermographic composition was prepared as described in Example 2. The photothermographic composition contained the following components:

| silver salt dispersion containing the silver salt of ABT (prepared as described in Example 1C) | 4.0 ml |
|---|---|
| silver bromoiodide emulsion (2.5 mole % iodide, 0.06 micron particle size, diluted 1:4 with distilled water). (The emulsion was diluted to provide about 13 mg. of Ag per ml.). | 0.7 ml |
| hydroquinone (10% by weight in methanol) | 0.7 ml |
| surfactant (Surfactannt 10G, 10% by weight in distilled water) | 0.2 ml |
| guanidinium trichloroacetate (5% by weight in distilled water) | 1.0 ml |
| distilled water | 1.4 ml |

The photothermographic composition was coated on a paper support at a 4 mil wet coating thickness to provide a photothermographic element. The photothermographic layer was permitted to dry and then imagewise exposed as described in Example 6. The resulting latent image was developed by heating the photothermographic element on a metal block at a temperature of 165° C. for 15 seconds. The developed image had a brown tone. The image had 5 visible developed steps with a maximum visual reflection density of 0.91 and a minimum density of 0.10. The minimum density areas (background areas) of the developed material were stable to light. No measurable increase in density was observed after exposure of the processed element for 24 hours at 120 foot candles of illumination.

EXAMPLE 11

Use of acrylamide polymer overcoat

A dispersion containing the silver salt of ABT prepared as described in Example 1C was used in this example. A photothermographic composition was prepared as described in Example 2 with the following components:

| silver salt dispersion containing the silver salt of ABT (prepared as described in Example 1C) | 4.0 ml |
|---|---|
| silver bromoiodide gelatino emulsion (2.5 mole % iodide, 0.06 micron particle size, diluted 1:4 with distilled water). (The emulsion was diluted to provide about 13 mg. of Ag per ml.). | 0.7 ml |
| tertiary-butylhydroquinone (10% by weight in methanol) | 0.35 ml |
| surfactant (Surfactant 10G, 10% by weight in distilled water) | 0.2 ml |
| distilled water | 2.8 ml |

The resulting photothermographic composition was coated at a 4 mil wet thickness on a paper support. The resulting photothermographic layer was permitted to dry and then overcoated at a 4 mil wet coating thickness with the following composition:

| poly(acrylamide-co-1-vinylimidazole) (weight ratio 90:10) (5% by weight solids in distilled water) | 4.0 ml |
|---|---|
| tertiary-butylhydroquinone (10% by weight in methanol) | 0.35 ml |
| surfactant (Surfactant 10G, 10% by weight in distilled water) | 0.2 ml |
| distilled water | 3.5 ml |

The resulting coating was permitted to dry to provide the desired photothermographic element. The element was imagewise exposed as described in Example 7 and the resulting latent image was developed and stabilized by heating the element on a metal block at 155° C. for 30 seconds. The resulting developed image had a brown-black tone with 6 visible developed steps and a visual maximum reflection density of 1.00 and a minimum density of 0.37. The image was exposed after processing to 120 foot candles of light for 24 hours. This produced an increase in minimum density of only 0.03 density units.

This illustrated that in addition to providing such advantages as resistance to abrasion marks, the described acrylamide polymer overcoat substantially lowers the processing conditions required to produce essentially complete stabilization to post-processing printout.

EXAMPLE 12

Use of the silver salt of 3-amino-5-(p-methoxy)benzylthio-1,2,4-triazole in a photothermographic material A silver salt dispersion was prepared as follows: 4.74 grams (0.02 mole) of 3-amino-5-(p-methoxy)benzylthio-1,2,4-triazole (referred to herein as AMBT) and 4.0 grams of deionized photographic gelatin were dissolved with heating in 30 milliliters of ethanol and 130 milliliters of distilled water. To this solution in a water jacketed mixing container, maintained at 55° C., was rapidly added a solution of 3.4 grams (0.02 mole) of silver nitrate in 40 milliliters of distilled water while mixing the composition rapidly. The mixing speed was increased and blending was continued for 40 minutes followed by cooling the composition to about 19° C. The final dispersion was adjusted to 233 grams (11.6 kilograms per silver mole) with distilled water. The silver salt dispersion had a pH of 2.1 and a pAg of 4.9.

A photothermographic composition was prepared by mixing the following components:

| silver salt dispersion containing the silver salt of AMBT (prepared as described above) | 4.0 ml |
|---|---|
| silver bromoiodide gelatino emulsion (2.5 mole % iodide, 0.06 micron particle size, diluted 1:4 with distilled water). (The emulsion was diluted to provide about 13 mg. of Ag per ml.). | 0.7 ml |
| ascorbic acid (10% by weight in distilled water) | 0.7 ml |
| surfactant (Surfactant 10G, 10% by weight in distilled water) | 0.2 ml |
| 3-amino-5-(p-methoxy)benzylthio-1,2,4-triazole (5% by weight in methanol) | 8.0 ml |

| | |
|---|---|
| -continued | |
| distilled water | 1.6 ml |

The final photothermographic composition contained a ligand to silver ion molar ratio of 1.4. The composition was coated at a 4 mil wet coating thickness on a paper support. The resulting layer was permitted to dry to provide the desired photothermographic element. The element was then imagewise exposed as described in Example 7 and the resulting latent image was developed by heating the element on a metal block at 155° C. for 30 seconds. The resulting developed image had a brown tone and 7 developed density steps with a visual maximum reflection density of 0.91 and a minimum density of 0.09.

The developed image was exposed for 24 hours to 120 foot candles of illumination. The $D_{min}$ area had only 0.03 density unit increase after this illumination.

The procedure was repeated with the exception that the latent image was developed by heating the element at a temperature of 175° C. for 10 seconds. A similar image was developed and had similar image stability to light after processing.

This illustrated that the silver salt of AMBT provided stabilization at either lower processing temperatures or shorter processing times than those required with compositions containing the silver salt of ABT.

EXAMPLE 13

Use of the silver salt of 3-amino-5-(p-chloro)benzylthio-1,2,4-triazole in a photothermographic material A. Preparation of silver salt of 3-amino-5-(p-chloro)benzylthio-1,2,4-thiazole The procedure described in Example 1C was repeated with the exception that 7.21 g. (0.03 mole) of 3-amino-5-(p-chloro)benzylthio-1,2,4-triazole (referred to herein as (ACBT) was used in place of 6.18 g. (0.03 mole) of ABT. The desired silver salt dispersion containing the silver salt of ACBT resulted from this preparation.

B. Photothermographic material containing the silver salt of 3-amino-5-(p-chloro)benzylthio-1,2,4-triazole A photothermographic composition was prepared by mixing the following components:

| | |
|---|---|
| silver salt dispersion containing the silver salt of ACBT, prepared as described above | 8.0 ml |
| silver bromoiodide gelatino emulsion (2.5% iodide, 0.06 micron particle size, diluted with water to provide about 13 mg. Ag/ml.) | 1.5 ml |
| t-butylhydroquinone (10% by weight in ethanol) | 1.5 ml |
| surfactant (Surfactant 10G, 10% by weight in distilled water) | 0.2 ml |
| distilled water | 1.0 ml |

The resulting composition was coated at 45° C. at a 6 mil wet coating thickness on a gelatin subbed poly(ethylene terephthalate) film support. The resulting photothermographic element was permitted to dry at ambient temperature and pressure. The element was then imagewise exposed to light as described in Example 2 to provide a developable latent image. The exposed element was then overall heated by contacting it with a metal block at 155° C. for 30 seconds. An image was developed having a purple tone with 5 visible steps and a visual diffuse maximum transmission density of 1.68 and a minimum density of 0.09.

The developed image was exposed to light (cool white fluorescent light) for 120 hours at 140 foot candles. An increase of only 0.07 in minimum density was observed.

EXAMPLE 14

Photothermographic film

A silver salt dispersion was prepared containing the silver salt of ABT as described in Example 1C. A photothermographic composition was prepared by mixing the following components:

| | |
|---|---|
| silver salt dispersion containing the silver salt of ABT (prepared as described in Example 1C) | 8.0 ml |
| silver bromoiodide gelatino emulsion (2.5 mole % iodide, 0.06 micron particle size, diluted 1:4 with distilled water). (The emulsion was diluted to provide about 13 mg. of Ag per ml.). | 1.4 ml |
| tertiary-butylhydroquinone (10% by weight in methanol) | 1.5 ml |
| surfactant (Surfactant 10G, 10% by weight in distilled water) | 0.3 ml |
| distilled water | 0.8 ml |

The resulting photothermographic composition was coated at a 6 mil wet coating thickness on a gelatin coated poly(ethylene terephthalate) film support at about 45° C. The photothermographic layer was permitted to dry. The resulting photothermographic element was then imagewise exposed as described in Example 2 to provide a developable latent image in the element. The latent image was developed and stabilized by heating the photothermographic film on a metal block at 175° C. for 30 seconds. A developed image resulted having a purple tone and 7 density steps. The developed image had a visual diffuse maximum density of 2.36 and a minimum density of 0.06. The clarity of the resulting photothermographic element was excellent, that is the non-image areas were completely transparent.

EXAMPLE 15

Silver salt dispersions of the following 1,2,4-triazole derivatives were prepared as described in Example 1C with the exceptions that the noted 1,2,4-triazole derivative was used in place of ABT and 60 ml of the described solvent combination was used in place of 30 ml due to the lower water solubility of the compounds:

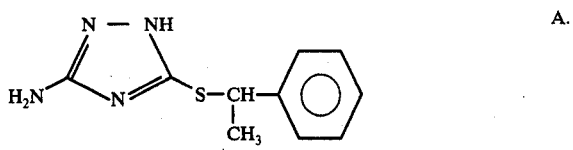

A.

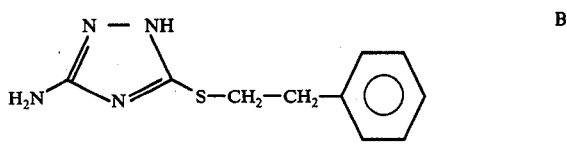

B.

-continued

C. 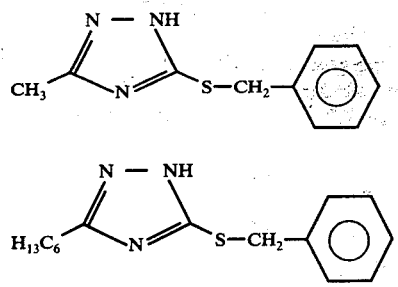

D.

The resulting silver salt dispersion in each instance was mixed with other components, then coated on a suitable support, dried, imagewise exposed to light and then overall heated as described in Example 2. The results obtained with each silver salt are as follows:

15A. — No developed image was obtained when the element was heated at 155° C. for 30 seconds.

15B. — A brown-black image having seven visible steps was obtained with a visual, maximum reflection density of 1.21 and a minimum density of 0.10 when the element was heated at 155° C. for 30 seconds. After processing the element was exposed to light. This produced an undesired increase in minimum density.

15C. — A developed image was produced having six visible steps with a visual, maximum reflection density of 0.50 and a minimum density of 0.17 when the element was heated at 155° C. for 30 seconds.

15D — A developed image was produced having seven visible steps. The image had a visual, maximum reflection density of 0.46 and a minimum density of 0.18 when the element was heated at 155° C. for 30 seconds.

EXAMPLE 16

Silver salts of the following 1,2,4-triazole derivatives were tested in a photothermographic material and process substantially as described in Example 2. In each case image development with no post-processing image stabilization was observed: (Z, Y and n refer to groups as designated in Formula I)

| Z | Y | n | image developed |
|---|---|---|---|
| H | -CH$_2$-⌬ | 1 | (weak image) |
| -CH$_3$ | -CH$_2$-⌬ | 1 | (weak image) |
| -C$_6$H$_{13}$ | -CH$_2$-⌬ | 1 | (weak image) |
| -NH$_2$ | -C$_4$H$_9$-n | 1 | (no image discrimination) |
| -NH$_2$ | -(CH$_2$)$_2$-⌬ | 2 | (good image) |
| -NH$_2$ | -CH$_2$-⌬-C≡N | 1 | (weak image) |
| -NH$_2$ | 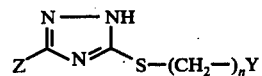 | 1 | (fair image) |
| -NH$_2$ | -CH(CH$_3$)-⌬ | 1 | (no image) |

(comparative example)

The invention has been described in detail with particular reference to preferred embodiments thereof, but it will be understood that variations and modifications can be effected within the spirit and scope of the invention.

What is claimed is:

1. A photothermographic element comprising a support having thereon in reactive association
   (a) photosensitive silver halide,
   (b) an image-forming combination comprising
      (i) a silver salt of a 3-amino-1,2,4-mercaptotriazole represented by the formula:

$$\underset{Z}{\overset{N-NH}{\diagdown}}\underset{N}{\diagup}S-(CH_2-)_nY$$

wherein Y is aryl containing 6 to 12 carbon atoms; n is 0 to 2; and Z is hydrogen, hydroxyl or —NH$_2$; with
      (ii) a silver halide developing agent, and a polymeric binder.

2. A process of developing an image in an exposed photothermographic element as defined in claim 1 comprising heating said element to a temperature within the range of 125° C. to 200° C. until an image is developed.

3. A process as in claim 2 comprising heating said element to a temperature within the range of 140° C. to 200° C. for 2 to 60 seconds.

4. A photothermographic element as in claim 1 wherein Y is phenyl, p-methoxyphenyl, or p-chlorophenyl.

5. A photothermographic element as in claim 1 also comprising a base precursor.

6. A photothermographic element as in claim 1 also comprising a base precursor consisting essentially of a guanidinium salt.

7. A photothermographic element as in claim 1 also comprising an image toner.

8. A photothermographic element as in claim 1 also comprising an image toner consisting essentially of a 1-phenyl-2-tetrazoline-5-thione compound.

9. A photothermographic element as in claim 1 wherein the silver salt of the 3-amino-1,2,4-mercaptotriazole has a molar ratio of ligand to silver ion within the range of 0.5 to 3.0.

10. A photothermographic element as in claim 1 comprising, for each mole of photosensitive silver halide, 2.0 to 8.0 moles of said silver salt of 3-amino-1,2,4-mercaptotriazole, and 5.0 to 10.0 moles of said silver halide developing agent.

11. A photothermographic element comprising a support having thereon in reactive association (a) photosensitive silver halide,
(b) an image-forming combination comprising
   (i) a silver salt of 3-amino-5-benzylthio-1,2,4-triazole, and
   (ii) a phenolic silver halide developing agent, and
(c) a polymeric binder.

12. A process of developing and stabilizing an image in a photothermographic element as defined in claim 11 comprising heating said element to a temperature within the range of 140° C. to 200° C. for 2 to 60 seconds.

13. A photothermographic element comprising a support having thereon in reactive association
(a) photosensitive silver halide,
(b) an image-forming combination comprising
   (i) a silver salt of 3-amino-5-(p-methoxy)benzylthio-1H-1,2,4-triazole, and
   (ii) a silver halide developing agent, and
(c) a polymeric binder.

14. A process of developing and stabilizing an image in a photothermographic element as defined in claim 13 comprising heating said element to a temperature within the range of 140° C. to 200° C. for 2 to 60 seconds.

15. A photothermographic element comprising a support having thereon in reactive association
(a) photosensitive silver halide,
(b) an image-forming combination comprising
   (i) a silver salt of 3-amino-5-(p-chloro)benzylthio-1,2,4-triazole, and
   (ii) a silver halide developing agent, and
(c) a polymeric binder.

16. A process of developing and stabilizing an image in a photothermographic element as defined in claim 15 comprising heating said element to a temperature within the range of 140° C. to 200° C. for 2 to 60 seconds.

17. A photothermographic composition comprising
(a) photosensitive silver halide, and
(b) an image-forming combination comprising
   (i) a silver salt of a 3-amino-1,2,4-mercaptotriazole represented by the formula:

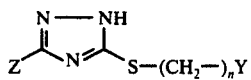

wherein Y is an aryl group containing 6 to 12 carbon atoms; n is 0 to 2; and Z is hydrogen, hydroxyl or $NH_2$; with
   (ii) a silver halide developing agent.

18. A photothermographic composition as in claim 17 also comprising a polymeric binder.

19. A photothermographic composition as in claim 17 wherein Y is phenyl, p-methoxyphenyl, or p-chlorophenyl.

20. A photothermographic composition as in claim 17 also comprising a base precursor.

21. A photothermographic composition as in claim 17 also comprising a base precursor consisting essentially of a guanidinium salt.

22. A photothermographic composition as in claim 17 also comprising an image toner.

23. A photothermographic composition as in claim 17 also comprising an image toner consisting essentially of a 1-phenyl-2-tetrazoline-5-thione compound.

24. A photothermographic composition as in claim 17 wherein the silver salt of the 3-amino-1,2,4-mercaptotriazole has a molar ratio of ligand to silver ion within the range of 0.5 to 3.0.

25. A photothermographic composition as in claim 17 comprising, for each mole of photosensitive silver halide, 2.0 to 8.0 moles of said silver salt of a 3-amino-1,2,4-mercaptotriazole, and 5.0 to 10.0 moles of said silver halide developing agent.

26. A photothermographic composition comprising
(a) photosensitive silver halide, and
(b) an image-forming combination comprising
   (i) a silver salt of 3-amino-5-benzylthio-1,2,4-triazole, and
   (ii) a phenolic silver halide developing agent.

27. A photothermographic composition as in claim 26 also comprising a gelatino binder.

28. A photothermographic composition as in claim 26 also comprising a toning agent consisting essentially of a 1-phenyl-2-tetrazoline-5-thione compound.

29. A photothermographic composition comprising
(a) photosensitive silver halide, and
(b) an image-forming combination comprising
   (i) a silver salt of 3-amino-5-(p-methoxy)benzylthio-1H-1,2,4-triazole, and
   (ii) a silver halide developing agent.

30. A photothermographic composition as in claim 29 also comprising a gelatino binder.

31. A photothermographic composition comprising
(a) photosensitive silver halide,
(b) an image-forming combination comprising
   (i) a silver salt of 3-amino-5-(p-chloro)benzylthio-1,2,4-triazole, and
   (ii) a silver halide developing agent.

32. A photothermographic composition as in claim 31 also comprising a gelatino binder.

* * * * *

UNITED STATES PATENT AND TRADEMARK OFFICE
CERTIFICATE OF CORRECTION

PATENT NO. : 4,123,274

DATED : October 31, 1978

INVENTOR(S) : Phillip D. Knight, Richard A. deMauriac and Patricia A. Graham

It is certified that error appears in the above-identified patent and that said Letters Patent are hereby corrected as shown below:

Column 10, line 7, "As especially" should read ---An especially---.

Column 19, line 27, "(Surfactannt 10G," should read --- (Surfactant 10G, ---.

Column 20, line 67, "8.0 ml" should read ---0.8 ml---.

*Signed and Sealed this*

*Twenty-fourth* Day of *April 1979*

[SEAL]

Attest:

RUTH C. MASON
*Attesting Officer*

DONALD W. BANNER
*Commissioner of Patents and Trademarks*